(12) United States Patent  
Takahashi (10) Patent No.: US 6,559,635 B2
(45) Date of Patent: May 6, 2003

(54) METHOD FOR NONDESTRUCTIVELY DETERMINING AGED DETERIORATION ACCOMPANYING CHANGE IN BRITTLENESS OF FERROMAGNETIC STRUCTION MATERIALS

(75) Inventor: Seiki Takahashi, Morioka (JP)

(73) Assignee: Iwate University, Iwate Pref (JP)

(*) Notice: Subject to any disclaimer, the term of this patent is extended or adjusted under 35 U.S.C. 154(b) by 0 days.

(21) Appl. No.: 10/172,875

(22) Filed: Jun. 13, 2002

(65) Prior Publication Data

US 2003/0006758 A1 Jan. 9, 2003

(30) Foreign Application Priority Data

Jun. 15, 2001 (JP) ......................... 2001-181135

(51) Int. Cl.⁷ .................... G01N 27/76; G01R 33/16
(52) U.S. Cl. ........................... 324/201; 324/228
(58) Field of Search ............................ 324/201, 228, 324/238, 262, 263, 248; 73/865.5

(56) References Cited

U.S. PATENT DOCUMENTS 5,311,125 A * 5/1994 Krause et al. ............ 324/201
5,506,500 A * 4/1996 Krause et al. ............ 324/201

* cited by examiner

Primary Examiner—Edward Lefkowitz
Assistant Examiner—Subhash Zaveri
(74) Attorney, Agent, or Firm—Knobbe Martens Olson & Bear LLP

(57) ABSTRACT

This invention is a method for nondestructively determining the deterioration of determining ferromagnetic materials by quantifying the change in brittleness with aging of the materials. This invention supposes acquirement of an embrittlement coefficient b by measuring a magnetic susceptibility $\chi_b$ of ferromagnetic materials under a magnetic field having a specified intensity H. And the coefficient b of the ferromagnetic materials is calculated by putting the intensity H and the susceptibility $\chi_b$ into an equation: $b = \chi_b H^2$. By the coefficient b, a correlation between the coefficient b and a referenced embrittlement factor of materials like said determining materials is obtained previously. The coefficient b of the determining materials in the initial and the deteriorated states is acquired. The factor corresponding to the coefficient b is obtained from the correlation. It is possible to quantify the change by comparing the values of the factor in the initial and deteriorated states.

3 Claims, 13 Drawing Sheets

METHOD FOR NONDESTRUCTIVELY DETERMINING AGED DETERIORATION ACCOMPANYING CHANGE IN BRITTLENESS OF FERROMAGNETIC STRUCTION MATERIALS

BACKGROUND OF THE INVENTION

1. Field of the Invention

The present invention relates to a method for nondestructively measuring and quantitatively determining deterioration in materials accompanying neutron irradiation, and the like, in a ferromagnetic construction material, or in a structure comprised of such materials.

2. Description of the Related Art

Conventional nondestructive inspection methods for aged material deterioration had generally aimed at investigating of initiation and growth of cracks in the material in almost every case. And thus, the direction of development in present nondestructive inspection methods lies in finding out produced cracks as minute as possible. Accordingly, with such a conventional nondestructive inspection method, it is practically impossible to inspect nondestructively aged deterioration of materials before the initiation of cracks.

By the way, it is generally considered that aged deterioration in a nuclear reactor pressure vessel goes on by combining precipitation of copper atoms, a dislocation loop etc, due to metal fatigue and neutron irradiation.

Another type of previous method is known for nondestructively determining deterioration of material strength due to aging of ferromagnetic construction materials or structures comprised of such construction materials. In this determining method, the coercive force and magnetic susceptibility in the range approaching to saturation of a determining object are measured.

Moreover, Japanese Patent Laid-open No. 2001-021538 discloses about aged deterioration due to metal fatigue of materials before the initiation of cracks. As described in this document, conventionally, the following nondestructive inspection method is known. That is, in the inspection method, the coercive force Hc and susceptibility coefficient c (Hereinafter referred to as a strength parameter c.) are measured. Then, from the strength parameter c, aged deterioration of strength in ferromagnetic construction materials or structures comprised of such the construction materials is determined.

Then, the inventor thought that if a nondestructive inspection for aged deterioration accompanying the change in brittleness of materials could be carried out by combining with the nondestructive inspection for aged deterioration accompanying the change in strength of materials, it would lead to much more improvement in the safety of a nuclear reactor pressure vessel. So the inventor focused attention on nondestructive inspection for determining aged deterioration accompanying the change in brittleness of materials.

However, it was impossible to apply the above-mentioned conventional nondestructive inspection method for aged deterioration of material strength to the nondestructive inspection method for aged deterioration accompanying the change in brittleness of materials due to precipitation of copper atoms and so on.

That is, conventional measuring objects are dislocations produced by metal fatigue. In such dislocations, anisotropic strain fields exist in the interior of materials. Therefore, it was possible to inspect nondestructive aged deterioration of materials by the conventional method measuring the coercive force Hc, because aged deterioration of material strength has much effect on the coercive force Hc.

On the other hand, in aged deterioration accompanying the change in brittleness of materials due to precipitation of copper atoms and so on, measuring objects are defects. The defects are atomic vacancies or interstitial atoms produced by irradiating neutron etc, or precipitation by heat treatment etc., and so on. In such defects, strain fields do not always exist in the interior of materials.

Therefore, aged deterioration accompanying the change in brittleness of materials hardly have much effect on the coercive force Hc. Accordingly, it was impossible to apply the method determining the coercive force Hc among above-mentioned nondestructive inspection methods for aged deterioration of material strength to determining of aged deterioration accompanying the change in brittleness of materials. Also, it was impossible to determine aged deterioration accompanying the change in brittleness of materials even by means of the conventional method obtaining the strength parameter c of the determining objects.

Accordingly, it is difficult to determine quantitatively embrittlement results from increase of precipitation of copper atoms and atomic vacancies.

Therefore, a new determining factor for examining quantitatively such embrittlement was necessary.

SUMMARY OF THE INVENTION

It is therefore a primary object of the present invention to provide an improved measurement method for nondestructively determining aged deterioration of ferromagnetic construction materials, which advantageously eliminates the above-mentioned problems of the prior art.

One aspect of the present invention resides in the method for nondestructively determining aged deterioration of ferromagnetic construction materials by quantifying the change in brittleness due to aging of the materials. The determining method according to the present invention includes the following steps.

One of the steps is to suppose to acquire an embrittlement coefficient b by measuring a magnetic susceptibility $\chi_b$ of the determining ferromagnetic construction material under a magnetic field having a predetermined magnetic field intensity H over a magnetic coercive force Hc of the determining material, and calculating an embrittlement coefficient b of the determining material by putting the magnetic field intensity H and the measured magnetic susceptibility $\chi_b$ of the determining material into an equation, $$b = \chi_b H^2 \tag{1}$$

Another one of the steps is to obtain a correlation between an embrittlement coefficient b and a referenced embrittlement factor of the same kind of ferromagnetic construction materials as the determining material previously, the value of the referenced embrittlement factor changes corresponding to the change in brittleness of the same kind of ferromagnetic construction materials.

Further one of the steps is to obtain the values of the embrittlement coefficient b of the determining ferromagnetic construction material in the initial state and the deteriorated state by aging.

Further one of the steps is to determine the values of the referenced embrittlement factor corresponding to the values of the embrittlement coefficient b respectively, based on the correlation.

Further one of the steps is to quantify the change in brittleness due to aging of the determining ferromagnetic construction material by comparing the values of the referenced embrittlement factor.

The principle of the present invention will be described below with reference to experimental test data. To clarify the correlation between the mechanical property and the magnetic property of steel materials, test pieces consisting of polycrystalline pure iron (99.992% purity) involving copper atoms (1.5 wt/%) were used. By heat treatment of test pieces in various temperatures, the copper atoms are precipitated in the test pieces.

By above-mentioned treatment of the test pieces, a precipitating quantity of the copper atoms and the size of precipitates can be changed corresponding to the change of temperatures and time in heat treatment.

By the way, it is known that copper atoms are precipitated at the heat treatment temperature, that is, the aging temperature, from 445° C. to 650° C., and such precipitation of cupper atoms in materials is related to hardness of materials.

In this way, precipitation of copper atoms is related to hardness in materials because the hardness of steel materials increases by the precipitation of copper atoms preventing the movement of dislocations.

Figure 4:
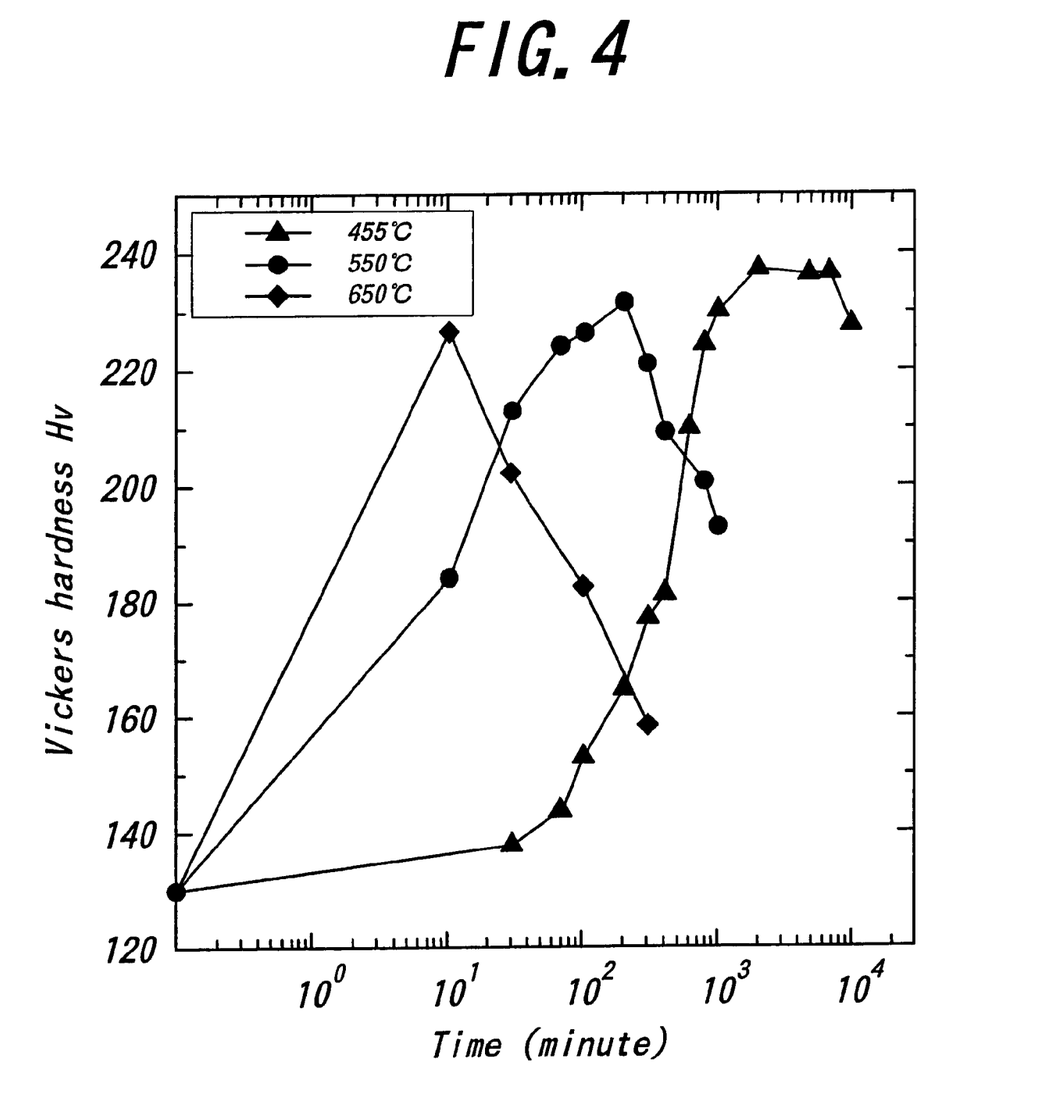
FIG. 4 is a graph showing the relation between aging time (minutes) and Vickers hardness (Hv) accompanying the change of precipitation of copper atoms in accordance with test results by use of test pieces heat-treated under the aging temperatures of 455° C., 550° C. and 650° C., respectively.

Then, in this experiment, as a result of test pieces heat-treated at each temperature (aging temperatures: 455° C., 550° C., 650° C.), as shown in FIG. 4, the correlation of heat treatment time (minute) and hardness (Vickers hardness Hv) was obtained in each temperature. Here, in FIG. 4, it is plotted in solid triangles (▲) about the test piece heat-treated at 455° C., it is plotted in solid circles (●) about the test piece heat-treated at 550° C., and it is plotted in solid diamonds (♦) about the test piece heat-treated at 650° C., respectively.

According to this result, for example, in the test piece heat-treated at 455° C., it turns out that precipitation of copper atoms progresses most in aging time for $2.0 \times 10^3$ to $7.0 \times 10^3$ minutes.

In addition, in the above-mentioned experiment, the copper atoms are precipitated by heat treatment in the test pieces. This is because it is generally thought that, when a neutron is irradiated in a pressure vessel, copper atoms, which migrate in the inner material composing of the pressure vessel, are precipitated and the precipitates embattle the pressure vessel.

In addition to this reason, there is also an idea that dislocation loops in the material are induced by neutron irradiation in a pressure vessel and these dislocation loops contribute to the embrittlement of the pressure vessel. Therefore, in the above-mentioned experiment, test pieces are heat-treated as what is replaced with the neutron irradiation to the pressure vessel leading to precipitation of copper atoms, and, thereby, the copper atoms in the material are precipitated.

Figure 5:
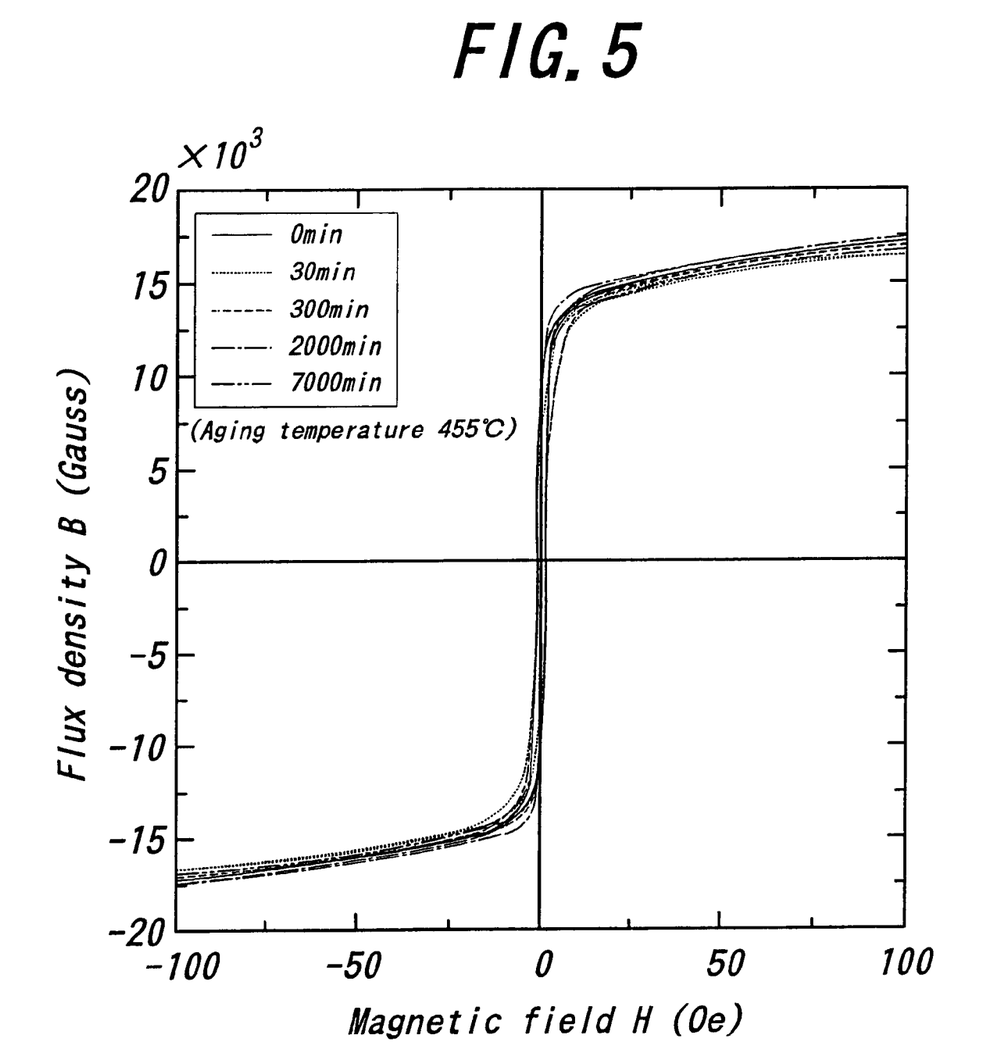
FIG. 5 is a graph showing the hysteresis loops of test pieces heat-treated under aging temperature of 455° C. in aging time of 0 min. (minutes), 30 min., $3.0 \times 10^2$ min., $2.0 \times 10^3$ min. and $7.0 \times 10^3$ min., respectively.
Figure 6:
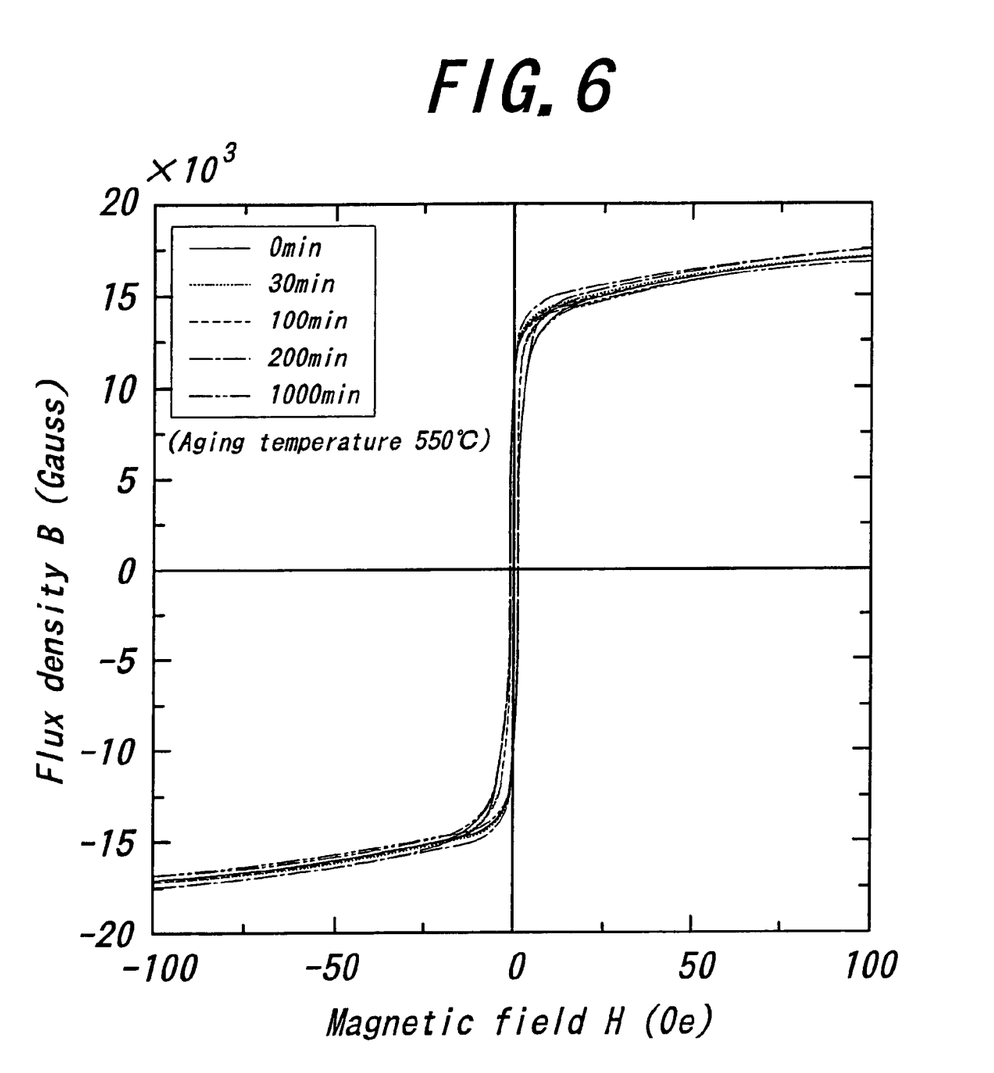
FIG. 6 is a graph showing the hysteresis loops of test pieces heat-treated under aging temperature of 550° C. in aging time of 0 min., 30 min., $1.0 \times 10^2$ min., $2.0 \times 10^2$ min. and $1.0 \times 10^3$ min., respectively.

FIGS. 5 and 6 are explanation diagrams showing the hysteresis loop obtained from the loop test of the test pieces, in which the copper atoms are precipitated by heat treatment. Here, FIG. 5 shows the change of the hysteresis loop characteristics accompanying the copper precipitation by heat treatment in aging time (0 min., 30 min., $3.0 \times 10^2$ min., $2.0 \times 10^3$ min., $7.0 \times 10^3$ min.) under aging temperature of 455° C. Also, FIG. 6 shows the change of the hysteresis loop characteristics accompanying the copper precipitation by heat treatment in aging time (0 min., 30 min., $1.0 \times 10^2$ min., $2.0 \times 10^2$ min., $1.0 \times 10^3$ min.) under aging temperature of 550° C. In the hysteresis loops obtained by hysteresis loop characteristic test of both of FIGS. 5 and 6, significant change is not seen depending on the change of aging time.

However, on study of the inventor, when analysis is performed as below, it was proved that the change (change of brittleness) in the precipitation state of copper atoms in the material accompanying the change of aging conditions (aging time, aging temperature) based on the hysteresis loop could be expressed quantitatively.

From the hysteresis loop as shown in FIG. 5, the relation of the logarithm of magnetic susceptibility $\chi_b$ (=flux density B (Gauss)/magnetic field intensity H (Oe)) to the logarithm of the magnetic field intensity H is plotted. Thereby, the relationships as shown in FIGS. 7 and 8 are obtained.

Figure 7:
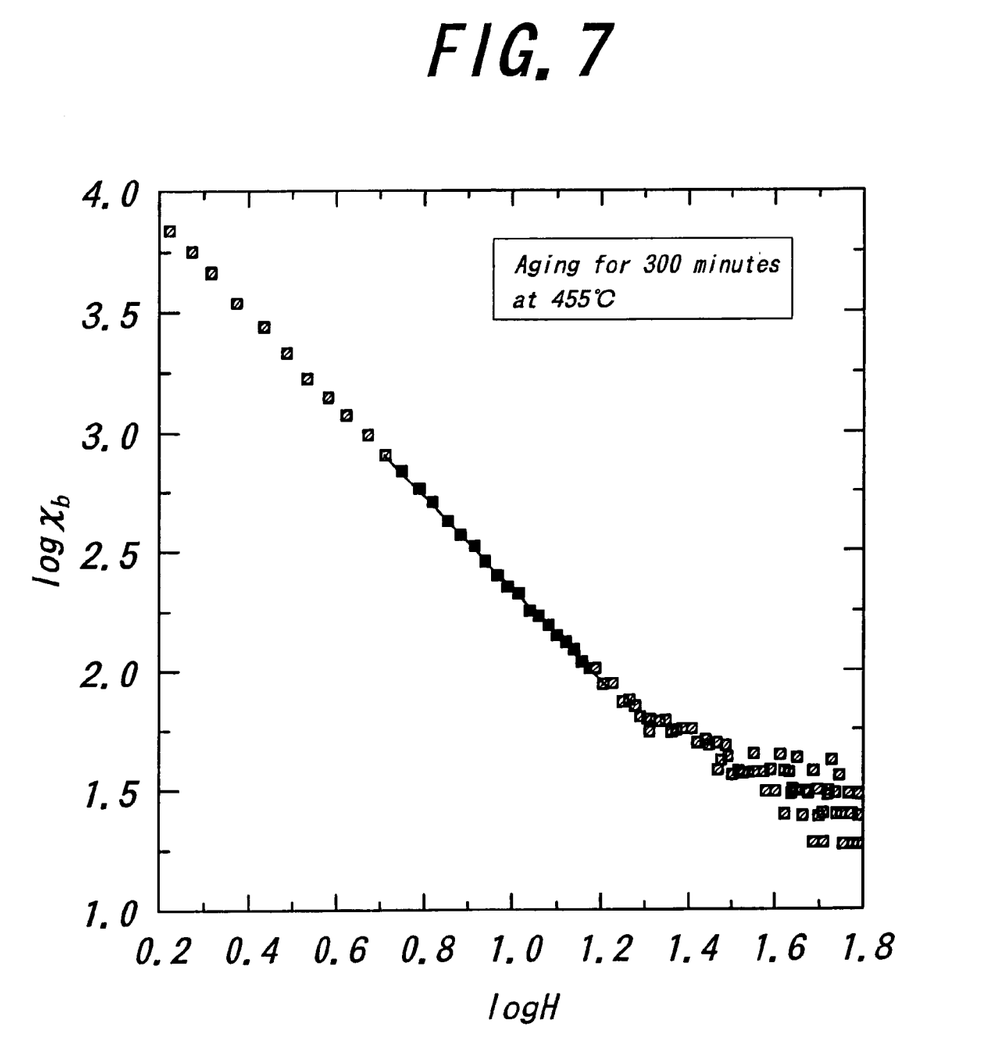
FIG. 7 is a graph showing the relationship between the common logarithm of the magnetic susceptibility $\chi_b$ and the common logarithm of the magnetic field intensity H in Fe-1.5% Cu alloy aged for $3.0 \times 10^2$ min. at 455° C.
Figure 8:
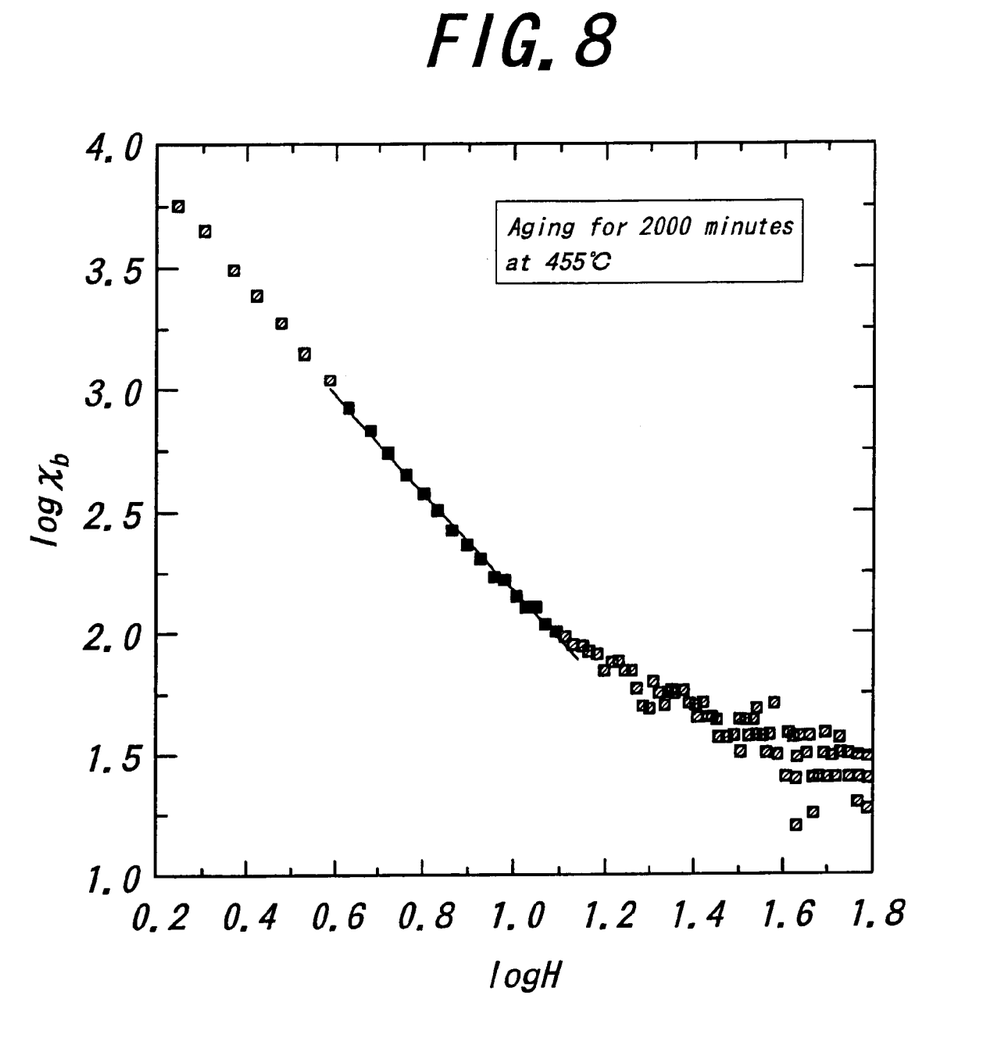
FIG. 8 is a graph showing the relationship between the common logarithm of the magnetic susceptibility $\chi_b$ and the common logarithm of the magnetic field H in Fe-1.5% Cu alloy aged for $2.0 \times 10^3$ min. at 455° C.

Here, FIG. 7 illustrates the relationship in a test piece aged for aging time $3.0 \times 10^2$ minutes under aging temperature of 455° C., and FIG. 8 illustrates the relationship about a test piece aged for aging time $2.0 \times 10^3$ minutes under aging temperature of 455° C.

In addition, in each of FIGS. 7 and 8, the logarithm is illustrated using common logarithm (log base 10), and the straight line of gradient of −2 being best match with related diagram is illustrated. And from the relationships (the straight lines of gradient of −2) shown by FIGS. 7 and 8, the relationship as shown with the next equation is obtained.

$$\log (\chi_b) = \log (b) - 2 \log (H) \quad (2).$$

And from this equation (2), the next equation is obtained.

$$\chi_b = b/H^2 \quad (3).$$

This equation can change into the equation (1) described previously. Therefore, log (b) is determined from the gradient of −2 (a straight line of the equation (2)) shown in FIGS. 7 and 8. Therefore, the embrittlement coefficient b can be obtained from the values of the log (b).

Figure 9:
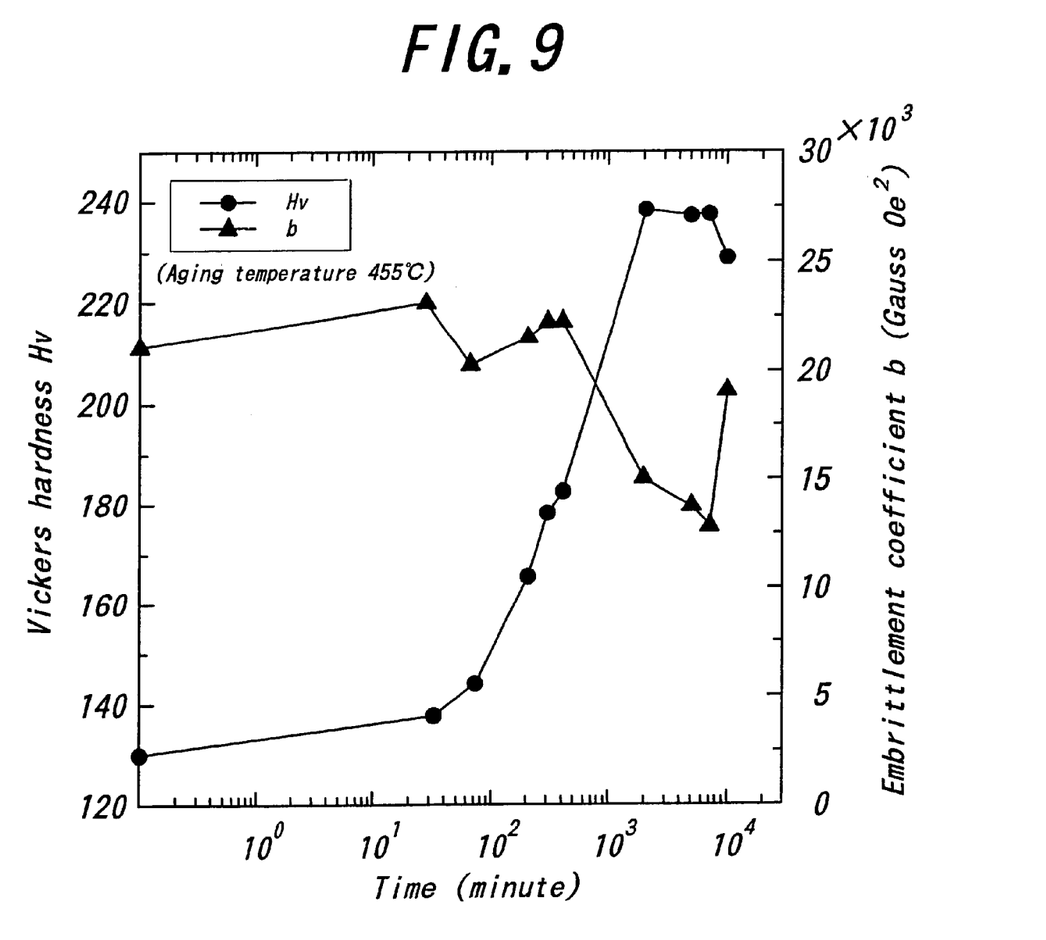
FIG. 9 is a graph showing the relationship between Vickers hardness Hv and the embrittlement coefficient b (Gauss Oe$^2$) versus aging time (minutes) in Fe-1.5% Cu alloy aged at 455° C.
Figure 10:
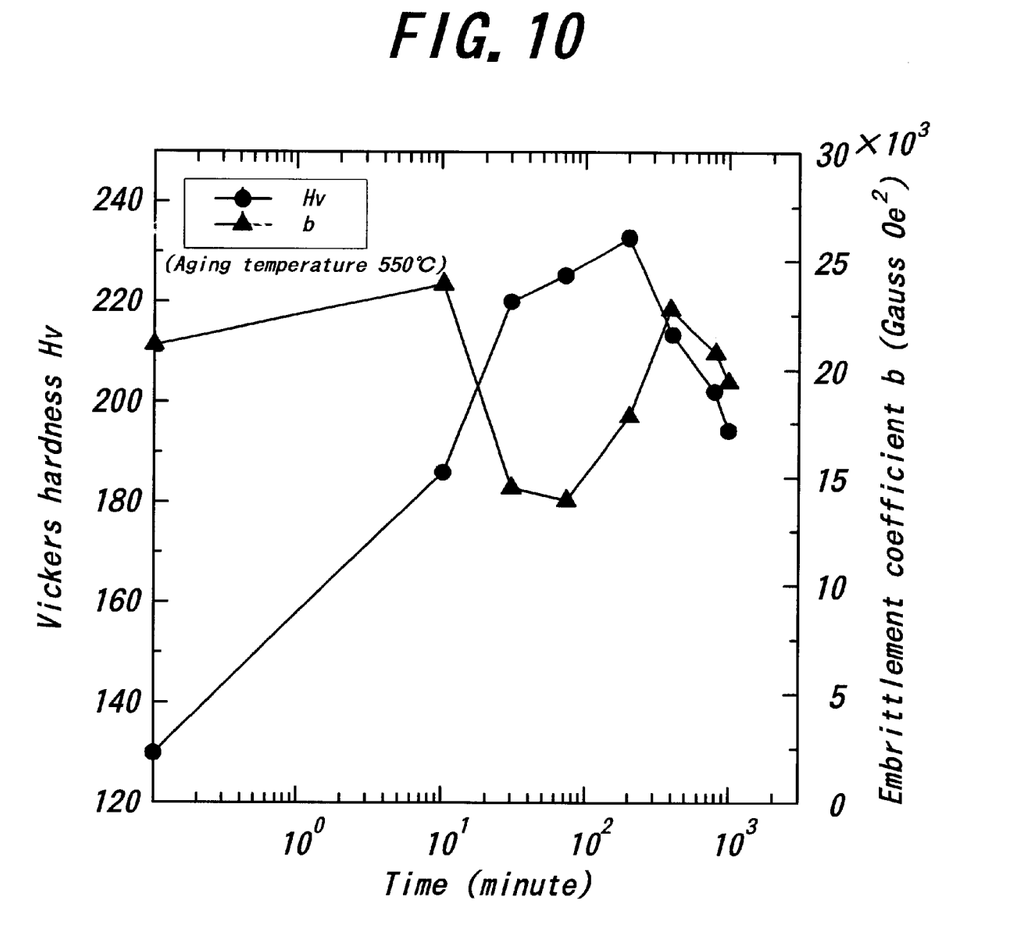
FIG. 10 is a graph showing the relationship between Vickers hardness Hv and the embrittlement coefficient b (Gauss Oe$^2$) versus aging time (minutes) in Fe-1.5% Cu alloy aged at 550° C.
Figure 11:
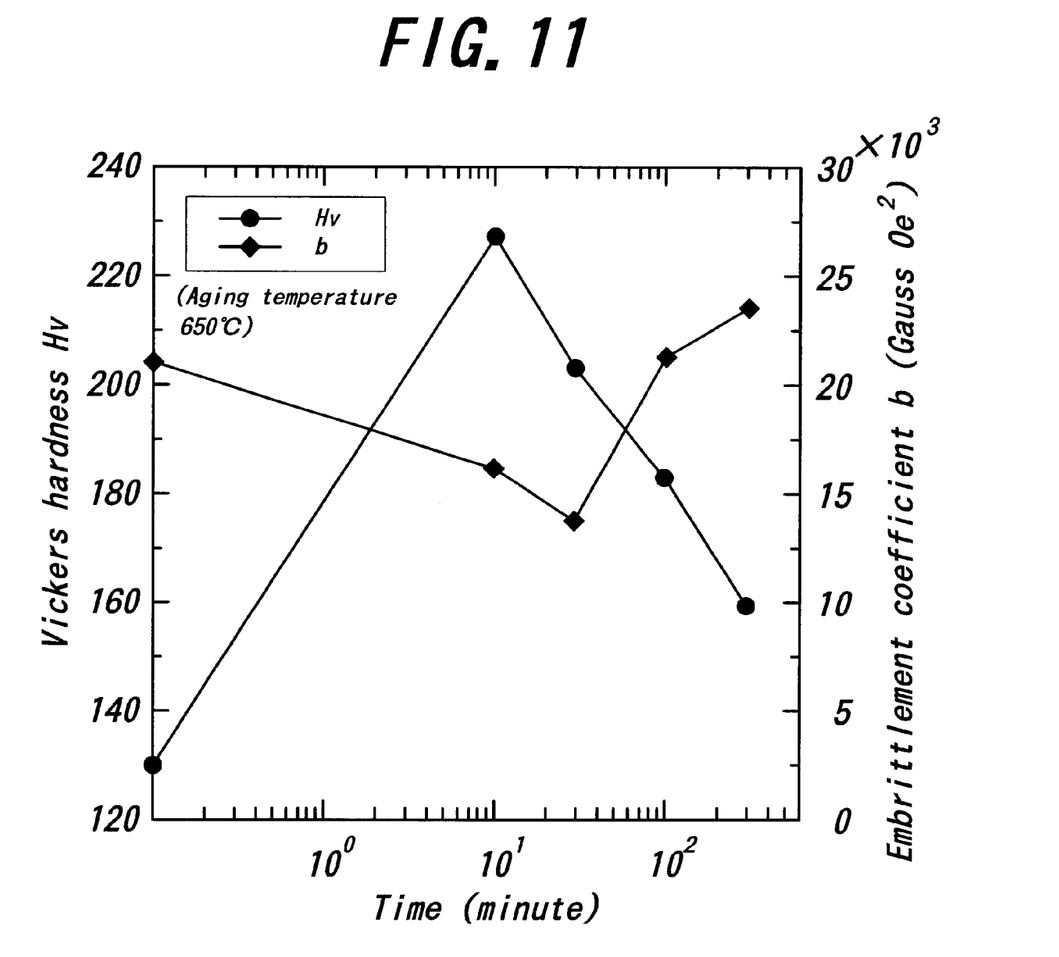
FIG. 11 is a graph showing the relationship between Vickers hardness and the embrittlement coefficient b (Gauss Oe$^2$) versus aging time (minutes) in Fe-1.5% Cu alloy aged at 650° C.

FIGS. 9, 10 and 11 are explanatory diagrams illustrating, by comparing with Vickers hardness Hv, the relation between the embrittlement coefficient b and aging time obtained from above-mentioned means. Here, in FIG. 9 is shown the relationship under aging temperature of 455° C., in FIG. 10 is shown the relationship under aging temperature of 550° C., and in FIG. 11 is shown the relationship under aging temperature of 650° C.

According to these relationships, it became clear by experiment of the inventor that the phenomenon that the value of the embrittlement coefficient b decreases and takes the local minimum and the phenomenon that Vickers hardness Hv increases and takes the local maximum correspond well according to aging time about all of FIGS. 9 to 11. Then, if the relation between the embrittlement coefficient b and Vickers hardness Hv is illustrated from the related diagram expressed with FIGS. 9 to 11, the distribution of the values shown in FIG. 12 will be obtained, and the correlation as shown by the curve in FIG. 12 will be obtained.

Figure 12:
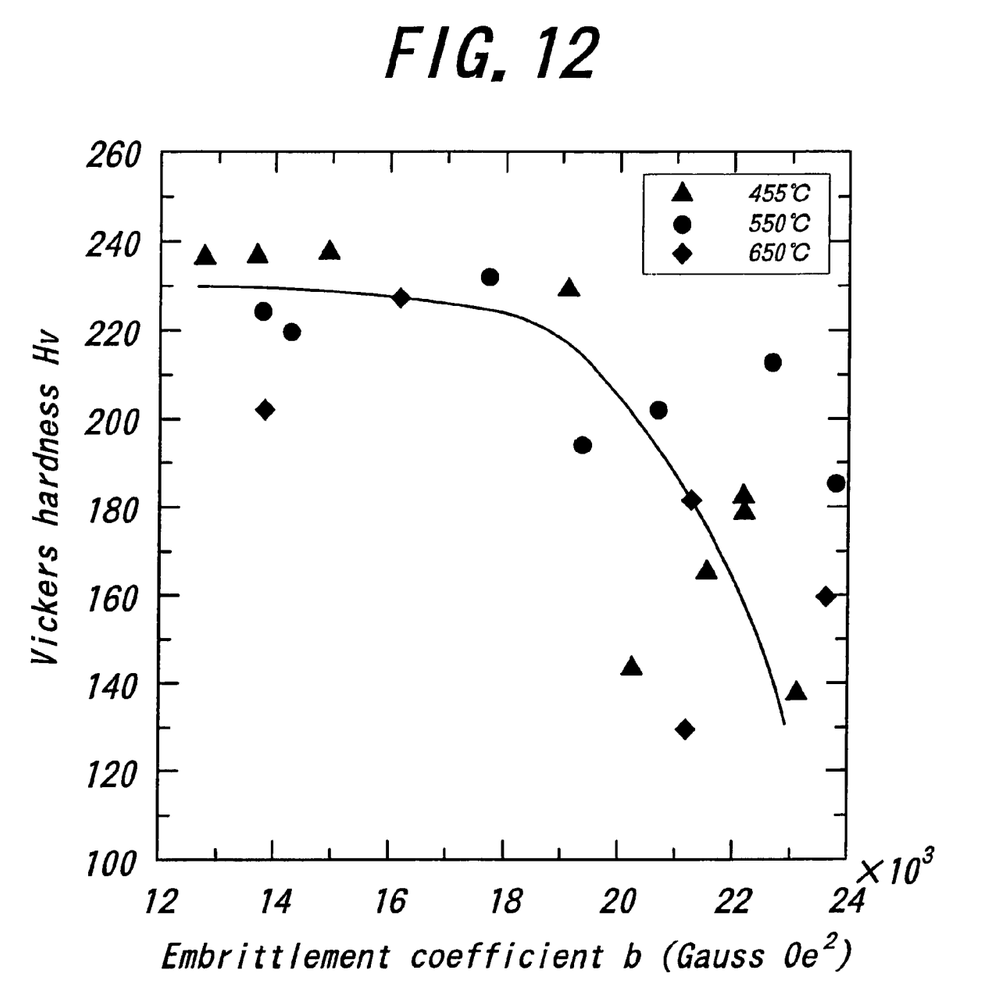
FIG. 12 is a graph showing the relationship between Vickers hardness Hv and the embrittlement coefficient b (Gauss Oe$^2$) in Fe-1.5% Cu alloy aged at 455° C., 550° C. and 650° C.; respectively.

In addition, in FIG. 12, it is plotted in solid triangles (▲) about the test piece heat-treated at 455° C., it is plotted in solid circles (●) about the test piece heat-treated at 550° C., and it is plotted in solid diamonds (♦) about the test piece heat-treated at 650° C., respectively.

By the way, according to the above-mentioned FIG. 4, it turns out that Vickers hardness Hv shows it gets to the local maximum (maximum) near for $5.0 \times 10^3$ minutes at the aging temperature of 455° C., the local maximum (maximum) near for $2.0 \times 10^2$ minutes at the aging temperature of 550° C., the local maximum (maximum) near for 10 minutes at the aging temperature of 650° C., respectively. This is based on the following reason. That is, copper atoms are precipitated with the help of atomic vacancies and the precipitate density gets to a peak in the initial stage of the precipitation. And when the test piece is aged further more, the copper precipitate grows up gradually and the average distance of precipitates becomes large. And Vickers hardness Hv recovers. Accordingly, Vickers hardness Hv degrades. This reason indicates that when Vickers hardness Hv gets to a peak, brittleness will be highest (embrittlement will progress most).

From above-mentioned reason, it can turn out that Vickers hardness Hv changes corresponding to the change in brittleness of a ferromagnetic structure material, and such Vickers hardness Hv can be used as a referenced embrittlement factor. Therefore, concerning the ferromagnetic construction materials as the object for determining aged deterioration, the values of the embrittlement coefficient b of the material in the initial state and the aged state are obtained from the relationship as shown in FIG. 12. Then, values of the referenced embrittlement factor in the initial state and the aged state corresponding to the values of the embrittlement coefficient b are obtained from the correlation. Finally, the values of the referenced embrittlement factor are compared with each other. Thus, it is possible to determine quantitatively the change (extent of embrittlement) in brittleness due to aging of the ferromagnetic construction materials with the object for determining aged deterioration.

That is, according to the method of the present invention, the method is performed by using test pieces of ferromagnetic materials of the same kind as the ferromagnetic structure material by which the non-destructive test of aged deterioration is carried out previously.

Here, the correlation between the embrittlement coefficient b and a referenced embrittlement factor (Vickers hardness Hv in FIG. 12) for example as shown by the curve in FIG. 12 is determined, and the correlation is defined as a referenced correlation of the structure material.

By the same as the above-mentioned method, it is possible to obtain the embrittlement coefficients b in the initial state and the aged state of a ferromagnetic construction material, or of a structure (for example, a reactor pressure vessel etc.) comprised of such a material from the hysteresis loop obtained by performing hysteresis loop test. Then, the values of a referenced embrittlement factor corresponding to the embrittlement coefficients b can be obtained from the aforementioned referenced correlation. By comparing the values of the referenced embrittlement factor, the extent of brittleness in the measured structure can be determined quantitatively.

Moreover, according to the conventional method measuring Vickers hardness, even if it can acquire the information about the surface of materials, the information about brittleness in the interior of determining ferromagnetic structure materials cannot be acquired. On the contrary, according to the method of the present invention, the embrittlement coefficient b is obtained based on the hysteresis loop including the information about the interior of materials. Hereby, the present invention has an advantage that the information about the whole material also including the interior of a measured ferromagnetic structure material can be acquired against the conventional method.

In addition, in case of setting instruments (exiting coil, detecting coil) to a reactor pressure vessel etc. as the determining object, a hysteresis loop characteristic test can be performed, depending on the form of a measuring object, by winding directly coil round a determining object or by applying the magnetic yoke with winding coil to the measuring object. And from the obtained hysteresis loop, it is possible to obtain the embrittlement coefficient b.

That is, if a structure material is radiated by neutrons over the long term, vacancies in the interior of materials will increase, consequently, copper atoms will be precipitated and embrittlement in the structure material will advance. According to the method of this invention, it is possible to determine correctly the extent of substantial embrittlement due to such precipitation of copper atoms etc., and it is possible to determine nondestiuctively aged deterioration of materials.

Moreover, according to the method of this invention, it is possible to combine the above-mentioned former method by which aged deterioration of the material strength can be measured nondestructively and quantitatively by obtaining strength parameter c. If it does in this way, it can ask not only for the material strength but also for the change in brittleness quantitatively. Accordingly, it is possible to check simultaneously the change of the dislocation density accompanying metal fatigue, neutron irradiation, etc., and aged deterioration accompanying the material strength and the change in brittleness can be evaluated. In addition, the above-mentioned strength parameter c is defined by next equation:

$$c = \chi_c H^3 \qquad (4).$$

Especially, it is supposed that aged deterioration of materials due to neutron irradiation in a reactor pressure vessel will advance by correlating atomic vacancies, interstitial atoms and increase of dislocation loops, etc. mutually.

Therefore, it is possible to obtain the embrittlement coefficient b in the measuring method for aged deterioration of the ferromagnetic structure material by the present invention, and values of strength parameter c in the conventional measuring method for aged deterioration of strength of the ferromagnetic structure material by above-mentioned equation (1) or equation (4) from the hysteresis loop, respectably.

So, it is possible to obtain the deteriorated information about strength and brittleness of materials respectably, and it is possible to separate increase of atomic vacancies, interstitial atoms and copper precipitation, etc. from deterioration due to dislocation loops in material strength.

Also, as for the nondestructive determining method for aged deterioration accompanying the change in brittleness of ferromagnetic construction materials in the present invention, the referenced embrittlement factor may be hardness. According to the present invention, a hardness corresponding to the value of the embrittlement coefficient b can be obtained from the next equation showing the correlation between embrittlement coefficient b and hardness:

$$Hv = f(b) \qquad (5).$$

And as mentioned above, it is known that hardness corresponds to the change in brittleness of materials. Accordingly, the quantitative value of the change in brittleness of materials can be calculated certainly from Vickers hardness Hv corresponding to the embrittlement coefficient b.

DESCRIPTION OF THE PREFERRED EMBODIMENTS

Figure 1:
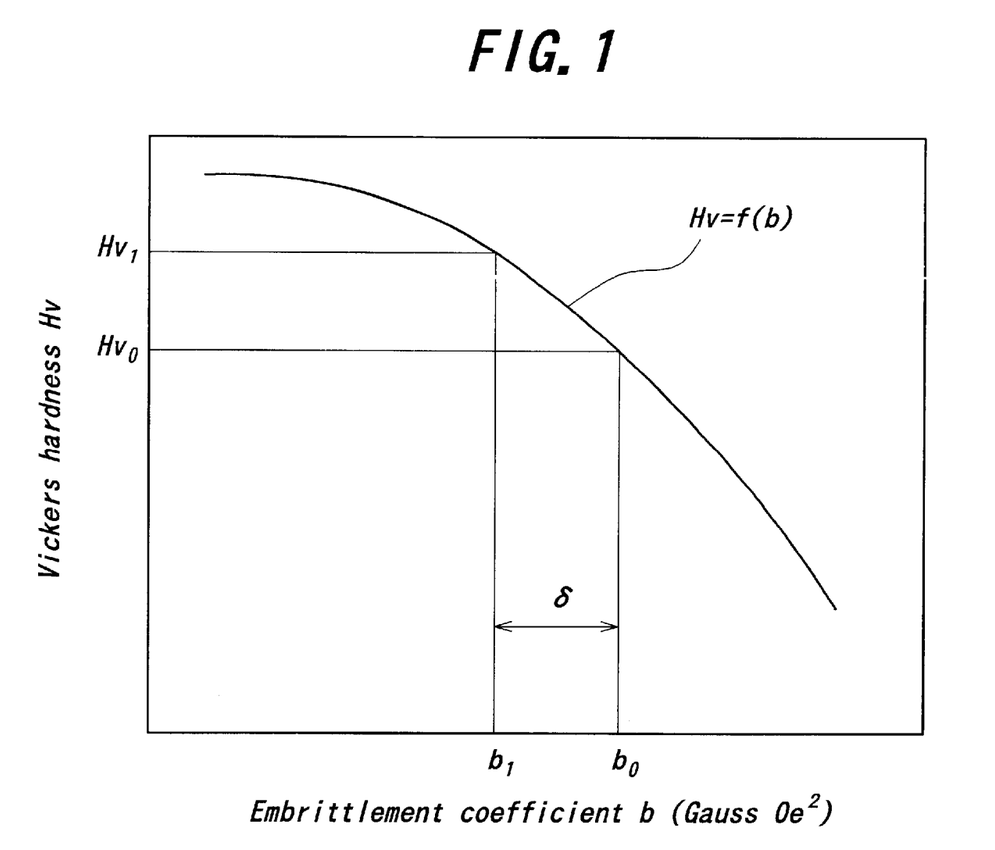
FIG. 1 is a view showing isothermal aging behavior, which exemplifies the correlation between the embrittlement coefficient b (Gauss Oe$^2$) and a referenced embrittlement factor (Vickers hardness Hv) using in the first example of the nondestructive determining aged deterioration accompanying the change in brittleness of ferromagnetic construction materials.
Figure 2:
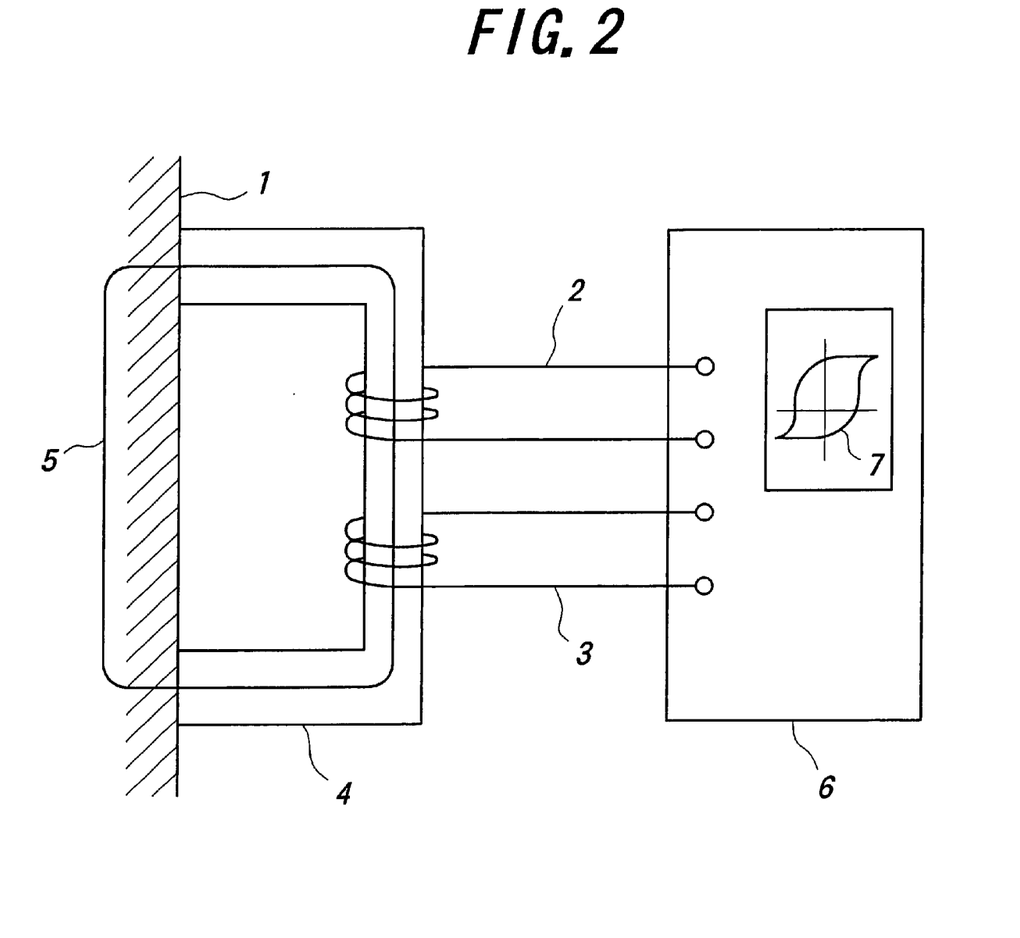
FIG. 2 is a view exemplifying the nondestructive determining method of the above embodiment.

The present invention will be described below in further detail, with reference to preferred embodiments shown in the attached drawings. FIG. 1 is a view exemplifying the correlation of the brittle coefficient b with a referenced embrittlement factor (Vickers hardness Hv) using in a first embodiment of the nondestructive determining aged deterioration accompanying the change in brittleness of ferromagnetic construction materials. And FIG. 2 is a view exemplifying the nondestructive determining method of the present embodiment. In drawings, reference numeral 1 denotes a determining ferromagnetic structure comprised of a ferromagnetic construction material with advanced embrittlement, 2 an excitation coil; 3 a flux detecting coil; and 4 a magnetic yoke on which these coils 2, 3 are wound.

Here, as shown in FIG. 2, the determining ferromagnetic structure 1 has a shape for which a direct winding of the coils 2 and 3 is impossible. Thus, the magnetic yoke 4 incorporating the excitation coil 2 and the flux detecting coil 3 is tightly applied onto the determining ferromagnetic structure 1 to form a closed magnetic circuit 5. The excitation coil 2 and flux detecting coil 3 are connected to a hysteresis loop measurement equipment 6. The hysteresis loop measurement equipment 6 may be one which is commercially available in the market.

Also the numeral 7 represents the characteristic magnetization of a hysteresis loop in the determining ferromagnetic structure 1 displayed on the hysteresis loop measurement equipment 6 as a consequence of performing this embodiment.

According to the method for nondestructive determining aged deterioration accompanying the change in brittleness of ferromagnetic construction materials by the present embodiment, excitation current is supplied to the excitation coil 2 from hysteresis loop measurement equipment 6. At this time, the voltage excited in a flux detecting coil 3 is led to hysteresis loop measurement equipment 6 and amplification and integration are carried out. As a result, the hysteresis loop 7 is acquired. In this embodiment, the magnetic susceptibility $\chi_b$ should just be obtained.

Therefore, the magnetic field intensity H from 1 K to 2 K Oe was required to make it magnetize to saturation magnetization and to measure in operation of the conventional method, on the other hand, in measuring method of this embodiment, it is sufficient for the measurement by the very low magnetic field intensity H of about 50 (Oe).

The hysteresis loop 7 acquired by applying the above-mentioned very low magnetic field intensity H includes the error due to a spread of three-dimensional magnetic circuit inside the determining ferromagnetic structure 1, or the influence of a demagnetizing factor. Therefore, it is necessary to obtain a fudge factor for acquiring the hysteresis loop in which such error has been removed.

However, this fudge factor can be calculated previously by the computer experiment using the known magnetostatic analysis technique or the mock-up imitated experimental real measurement system.

Accordingly, the value of the embrittlement coefficient b can be calculated by putting the values of the magnetic susceptibility $\chi_b$ and the magnetic field intensity H, which have been calculated by a pseudo-hysteresis loop in the magnetic field intensity H obtained as mentioned above, into the above-mentioned following equation (1):

$$b = \chi_b H^2.$$

And the value of Vickers hardness Hv can be obtained corresponding to the embrittlement coefficient b by putting the embrittlement coefficient b obtained in advance, which shows the correlation of the embrittlement coefficient b and Vickers hardness Hv as the referenced factor into the above-mentioned following equation (5):

$$Hv = f(b).$$

From the correlation between Vickers hardness Hv and the change in brittleness of materials, it is possible to determine the effective change of brittleness in the interior of materials composing the determining ferromagnetic structure in which brittleness has been advancing due to precipitation of copper atoms and so on.

The above-mentioned correlation Hv=f(b) is determined from the internal structure of materials, and this correlation Hv=f(b) can be calculated previously by measurement using the test piece of the material with the same kind of the determining ferromagnetic structure 1 as the ferromagnetic structure material with aged deterioration measurement object. And if the correlation Hv=f(b) was illustrated, the relation between the embrittlement coefficient b and Vickers hardness Hv would be expressed as a calibration curve Hv=f(b) shown in FIG. 1.

The calibration curve Hv=f(b) is determined as a referenced correlation of the determining ferromagnetic structure 1. And from this referenced correlation Hv=f(b), the value of Vickers hardness Hv (effective brittleness), which corresponds to the value of the embrittlement coefficient b obtained by the above-mentioned measurement, can be determined easily.

And on the occasion of evaluating aged deterioration accompanying the change in brittleness of materials, the hysteresis loop examination is similarly performed about the determining structure 1 before aged deterioration is generated, and the value of the embrittlement coefficient b is calculated by the same method as the above, and as shown in FIG. 1, let the value of this embrittlement coefficient b be the initial value $b_0$.

Also, the embrittlement coefficient b after aged deterioration, which is obtained by the above means, is set to $b_1$ (the embrittlement coefficient distance δ from the initial value $b_0$). And it is possible to obtain Vickers hardness $Hv_1$ corresponding to the embrittlement coefficient $b_1$ after aged deterioration and Vickers hardness $Hv_0$ corresponding to the initial value $b_0$.

Since these Vickers hardness $Hv_0$ and $Hv_1$ correspond to the change of brittleness, the change of brittleness due to aging in the determining structure 1 (extent of brittleness) can be determined nondestructively by comparing Vickers hardness $Hv_0$ with Vickers hardness $Hv_1$ nondestructively.

In addition, in the nondestructive determining method, the hysteresis loop test may run religiously for the determining structure 1 after aged deterioration and the change in brittleness of the material can be determined. Hereby, it is also possible to detect the state where the determining structure 1 is the weakest (minimum of the embrittlement coefficient b in FIG. 1).

Therefore, according to the method for nondestructive determining aged deterioration accompanying the change in brittleness of ferromagnetic construction materials in the present embodiment, the extent of aged deterioration accompanying the change in brittleness of ferromagnetic structure materials can be determined nondestructively and quantitatively by the following procedures.

That is, the value of the embrittlement coefficient b is calculated from the pseudo-hysteresis loop 7 obtained by the measurement in the given magnetic field intensity H in determining ferromagnetic structure materials. And the values $Hv_0$ and $Hv_1$ of Vickers hardness Hv corresponding to the values $b_0$ and $b_1$ of the embrittlement coefficient b, respectively, are obtained from the referenced correlation Hv=f(b) which shows the relation between the embrittlement coefficient b and Vickers hardness Hv which is illustrated in FIG. 1. And the values $Hv_0$ and $Hv_1$ of Vickers hardness Hv corresponding to the change in brittleness are compared.

Moreover in the method for nondestructive determining aged deterioration accompanying the change in brittleness of ferromagnetic construction materials of the present embodiment out of the pseudo-hysteresis loop 7 obtained by the measurement in the given magnetic field intensity H of determining ferromagnetic structure materials, by using the above-mentioned equation (4) $c=\chi_c H^3$, it is possible to calculate additionally the strength parameter c showing the extent of aged deterioration of strength of materials.

Therefore, according to the determining method of this embodiment, the extent of aged deterioration of all the structures comprised of ferromagnetic structure materials, such as a reactor pressure vessel, can be correctly inspected nondestructively that is caused by the amount of precipitation of copper atoms, the increase of dislocation density and the change of those inside distributions of materials at the stage before the initiation of cracks. In addition, it can be measured by a small magnetic yoke and an easy equipment with the excitation power supply with a small capacity.

Figure 3:
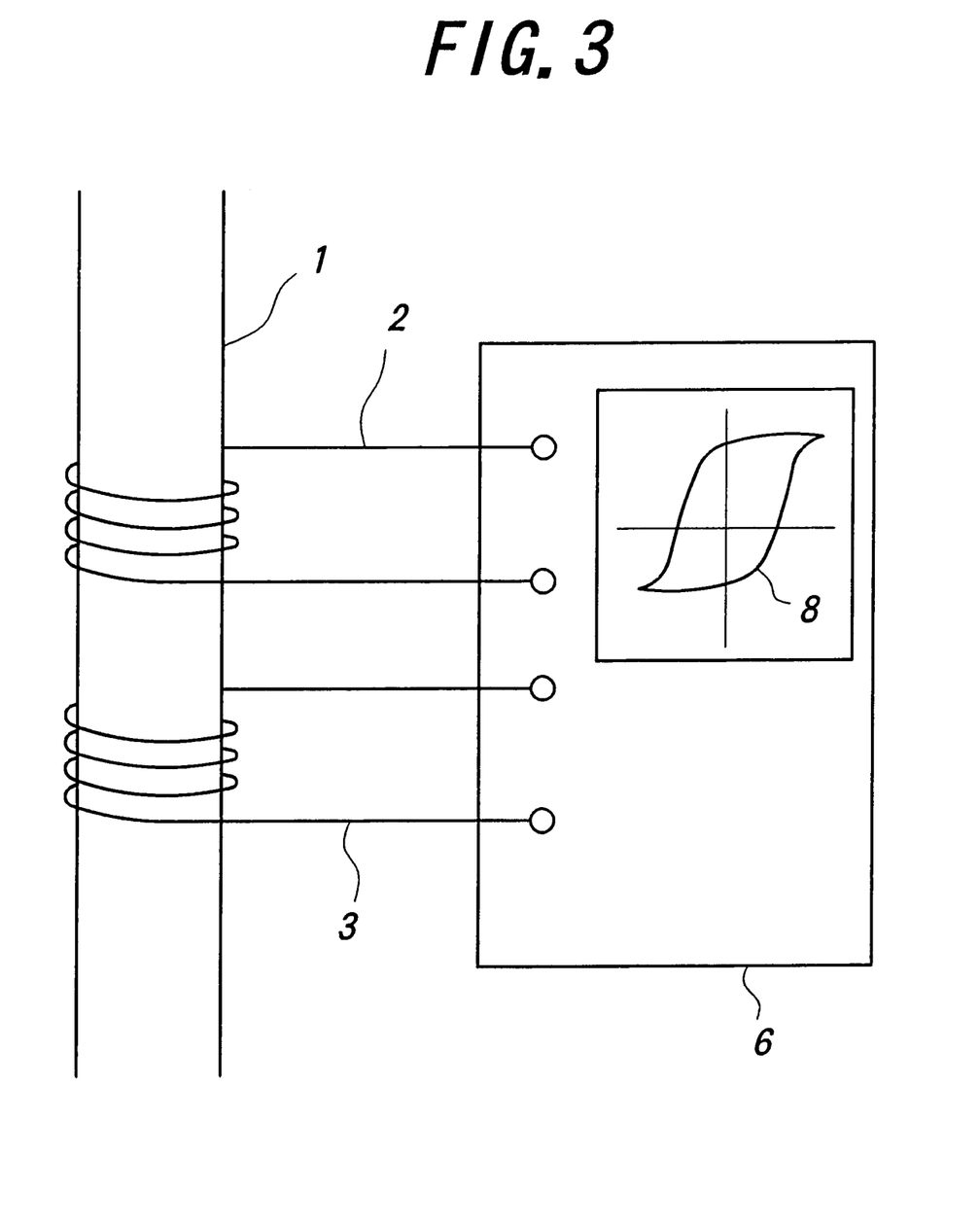
FIG. 3 is an illustration showing the second embodiment of the method for nondestructive determining aged deterioration accompanying the change in brittleness of ferromagnetic construction materials by the present invention.

FIG. 3 is an illustration showing the second embodiment of the method for nondestructive determining aged deterioration accompanying the change in brittleness of ferromagnetic construction materials by the present invention.

In contrast to the previous first embodiment, the determining structure 1 with advancing brittleness by precipitation of atoms etc. due to neutron irradiation etc. in the present embodiment has a shape that allows a magnetization coil 2 and a flux detecting coil 3 to be directly wound thereon, as typified by Charpy test pieces.

Thus, the excitation coil 2 and the flux detecting coil 3 are directly wound on the determining structure 1. Here, the hysteresis loop measurement equipment 6 may be one which is commercially available in the market such as the first previous embodiment. Also the numeral 8 represents the characteristic magnetization of a hysteresis loop in the determining ferromagnetic structure 1 displayed on the hysteresis loop measurement equipment 6 as a consequence of performing this embodiment.

In the present embodiment, the value of the embrittlement coefficient b is calculated from the hysteresis loop 8 acquired by the measurement at the very low magnetic field intensity H such as the first previous embodiment.

Also, the referenced correlation (not shown) between the embrittlement coefficient b and the Vickers hardness Hv as a brittleness factor is obtained previously by the same way as the referenced correlation of FIG. 1 obtained previously in the first embodiment.

And the secular brittleness change (extent of brittleness) of the ferromagnetic structure 1 can be determined nondestructively by comparing the value $Hv_0$ of the initial state with the value $Hv_1$ of aged deterioration in Vickers hardness Hv for the determining structure 1 from such the referenced correlation as the first embodiment.

Therefore, according to the method of the present embodiment, aged deterioration accompanying precipitation of copper atoms etc. in the determining ferromagnetic structure 1 can be inspected nondestructively like the previous embodiment with the shape of the determining structure on which the coil can be wound like a Charpy test piece equipped in the reactor pressure vessel. Furthermore, since there is not necessary to use a magnetic yoke, the simplification and the weight saving of equipments can be attained.

Figure 13:
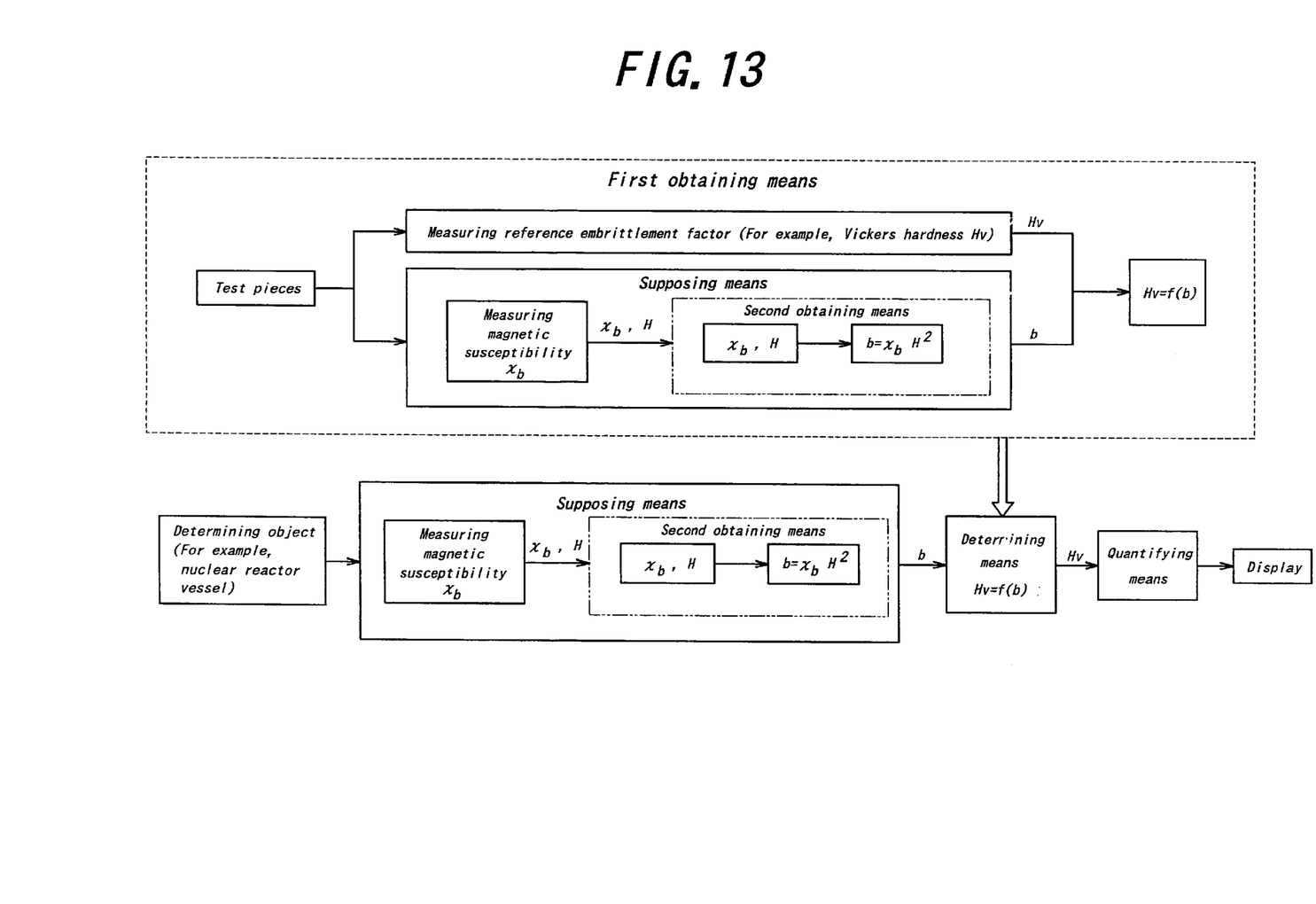
FIG. 13 is a block diagram showing the basic algorithm performed by the apparatus according to the present invention.

The basic algorithm performed in the determining method according to the present invention is schematically shown in FIG. 13. The apparatus for determining aged deterioration suitable for carrying out the determining method according to the present invention may be comprised of an appropriate workstation or a personal computer with incorporating programs based on the algorithms which is so prepared as to execute the above process steps.

While the present invention has been fully described above with reference to specific embodiments, they were presented solely for the purpose of illustration. Thus, a skilled person will readily appreciate that various changes or modifications may be made without departing from the scope of the invention as defined by the appended claims.

For example, although deterioration of the structure was determined in the above-mentioned embodiments, it goes without saying that deterioration of construction materials for the structure can be determined.

Moreover the determining equipment of aged deterioration can be comprised by combination means carrying out each process in the present invention.

While Vickers hardness Hv was used as a referenced embrittlement factor corresponding to the change in brittleness of materials in the above-mentioned the first and second embodiments, if it is the factor which changes corresponding to the change in brittleness of ferromagnetic materials, it will not be restricted to this. For example, the ductile-brittle transition temperature in Charpy impact test can be used as a referenced embrittlement factor. Also, for hardness, not only Vickers hardness but also hardness such as Rockwell hardness was used as a referenced embrittlement factor.

What is claimed is:

1. A method for nondestructively determining aged deterioration of a determining ferromagnetic construction material by quantifying the change in brittleness due to aging of the material, said method comprising the steps of:

supposing to obtain an embrittlement coefficient (b) by measuring a magnetic susceptibility ($\chi_b$) of said determining ferromagnetic construction material under a magnetic field having a predetermined magnetic field intensity (H) over a magnetic coercive force (Hc) of said determining material, and calculating the embrittlement coefficient (b) of said determining material by putting said magnetic field intensity (H) and said measured magnetic susceptibility ($\chi_b$) of said determining material into an equation, $$b = \chi_b H^2;$$

obtaining a correlation between the embrittlement coefficient (b) and a referenced embrittlement factor of the same kind of ferromagnetic construction materials as said determining material previously, the value of the referenced embrittlement factor changes corresponding to the change in brittleness of said same kind of ferromagnetic construction materials;

obtaining the values of said embrittlement coefficient (b) of said determining ferromagnetic construction material in the initial state and the deteriorated state by aging;

determining the values of said referenced embrittlement factor corresponding to said values of said embrittlement coefficient (b) respectively, based on said correlation; and quantifying the change in brittleness due to aging of said determining ferromagnetic construction material by comparing said values of said referenced embrittlement factor.

2. The measurement method according to claim 1, wherein said referenced embrittlement is hardness.

3. An apparatus nondestructively determining aged deterioration of a determining ferromagnetic construction material by quantifying the change in brittleness due to aging of the material, comprising:

supposing means for supposing acquirement of an embrittlement coefficient (b) by measuring a magnetic susceptibility ($\chi_b$) of said determining ferromagnetic construction material under a magnetic field having a predetermined magnetic field intensity (H) over a magnetic coercive force (Hc) of said determining material, and calculating an embrittlement coefficient (b) of said determining material by putting said magnetic field intensity (H) and said measured magnetic susceptibility ($\chi_b$) of said determining material into an equation, $$b = \chi_b H^2;$$

first obtaining means for obtaining a correlation between an embrittlement coefficient (b) and a referenced embrittlement factor of the same kind of ferromagnetic construction materials as said determining material previously, the value of the referenced embrittlement factor changes corresponding to the change in brittleness of the same kind of said ferromagnetic construction materials;

second obtaining means for obtaining the values of said embrittlement coefficient (b) of said determining ferromagnetic construction material in the initial state and the deteriorated state by aging;

determining means for determining the values of said referenced embrittlement factor corresponding to said values of said embrittlement coefficient (b) respectively, based on said correlation; and quantifying means for quantifying the change in brittleness due to aging of said determining ferromagnetic construction material by comparing said values of said referenced embrittlement factor.

* * * * *